United States Patent [19]

Shapiro

[11] 4,414,967
[45] Nov. 15, 1983

[54] INTERNAL FIXATION OF BONE, TENDON, AND LIGAMENTS

[75] Inventor: Jules S. Shapiro, Evanston, Ill.

[73] Assignee: Minnesota Mining and Manufacturing Company, St. Paul, Minn.

[21] Appl. No.: 275,896

[22] Filed: Jun. 22, 1981

[51] Int. Cl.³ .................. A61F 5/04; A61B 17/04
[52] U.S. Cl. .................. 128/92 B; 128/92 D; 128/92 E; 128/334 R; 227/DIG. 1
[58] Field of Search .............. 128/92 R, 92 B, 92 D, 128/92 E, 92 G, 334, 325; 227/19, DIG. 1

[56] References Cited

U.S. PATENT DOCUMENTS

| | | |
|---|---|---|
| 1,447,620 | 3/1923 | Lane et al. |
| 2,825,329 | 3/1958 | Caesar ................. 128/92 |
| 3,176,896 | 4/1965 | Mallina ............... 227/19 |
| 3,641,590 | 2/1972 | Michele ............... 3/1 |
| 3,822,818 | 7/1974 | Strekopytov et al. ...... 227/124 |
| 3,824,995 | 7/1974 | Gefacher et al. ......... 128/92 B |
| 3,875,936 | 4/1975 | Volz ................... 128/92 CA |
| 3,939,828 | 2/1976 | Mohr et al. ............ 128/92 B |
| 3,960,147 | 6/1976 | Murray ................ 128/92 B |
| 3,997,138 | 12/1976 | Crock et al. ........... 128/92 B |
| 4,011,863 | 3/1977 | Zickel ................. 128/92 BA |
| 4,041,939 | 8/1977 | Hall ................... 128/69 |
| 4,047,523 | 9/1977 | Hall ................... 128/69 |
| 4,047,524 | 9/1977 | Hall ................... 128/69 |
| 4,091,880 | 5/1978 | Troutner et al. ........ 128/92 EB |
| 4,146,022 | 3/1979 | Johnson et al. ......... 128/92 B |
| 4,180,196 | 12/1979 | Huiel et al. ........... 227/19 |
| 4,196,836 | 4/1980 | Becht .................. 128/334 R |
| 4,201,215 | 5/1980 | Crossett et al. ........ 128/335 |
| 4,217,902 | 12/1978 | Homsy .................. 128/92 G |
| 4,263,903 | 4/1981 | Griggs ................. 128/92 B |
| 4,272,002 | 6/1981 | Moshofsky ............. 227/19 |
| 4,278,091 | 7/1981 | Borzone ................ 128/92 B |

FOREIGN PATENT DOCUMENTS

| | | | |
|---|---|---|---|
| 2703529 | 8/1978 | Fed. Rep. of Germany .... | 128/92 B |
| 1558965 | 1/1980 | United Kingdom ........... | 128/92 B |
| 264613 | 6/1970 | U.S.S.R. ................. | 128/92 D |
| 271713 | 9/1970 | U.S.S.R. ................. | 128/92 B |
| 633522 | 4/1976 | U.S.S.R. ................. | 128/92 B |

OTHER PUBLICATIONS

Journal of Bone & Joint Surgery, May 1953, vol. 35-B#2, pp. 258-259, by G. K. McKee.
Article entitled "Minimal Internal Fixation of Tibial Fractures" by Frederick W. Rhinelander, M. D., appearing in the Mar.-Apr. 1975 issueof *Clinical Orthopaedics and Related Research*, No. 107, starting at p. 188.

*Primary Examiner*—C. Fred Rosenbaum
*Assistant Examiner*—C. W. Shedd
*Attorney, Agent, or Firm*—Donald M. Sell; James A. Smith; Robert W. Hoke, II

[57] ABSTRACT

A method of joining bone to bone, tendon to bone, and ligament to bone utilizes a power staple gun or a power rivet gun.

9 Claims, 12 Drawing Figures

U.S. Patent  Nov. 15, 1983  4,414,967
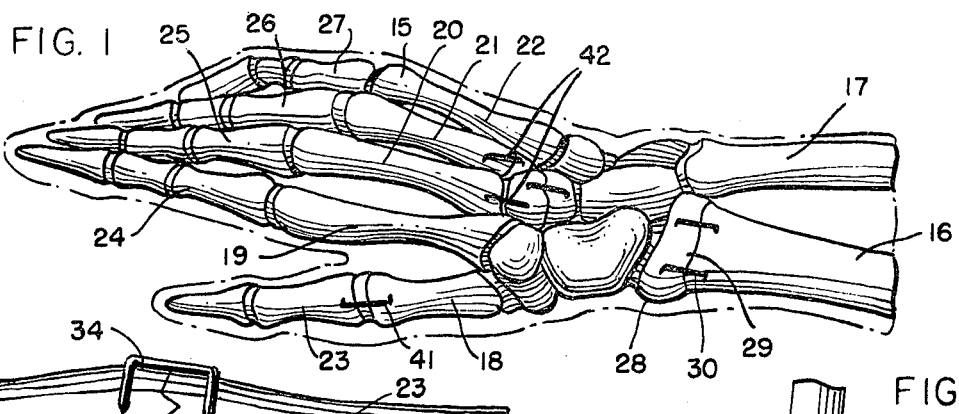
FIG. 1
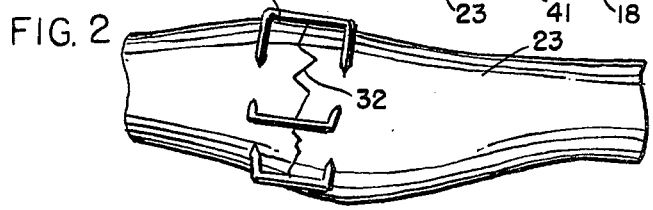
FIG. 2
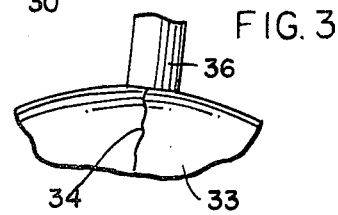
FIG. 3
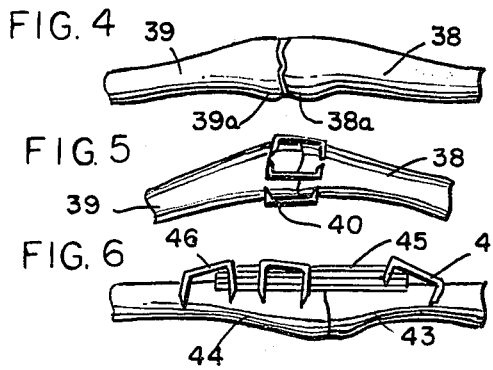
FIG. 4
FIG. 5
FIG. 6
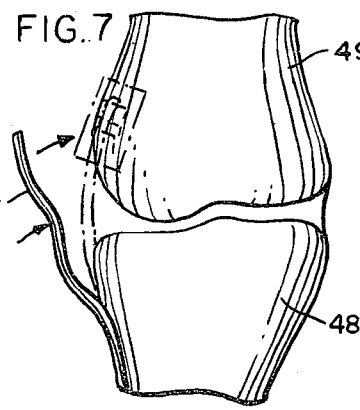
FIG. 7
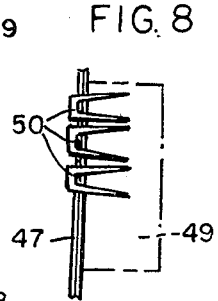
FIG. 8
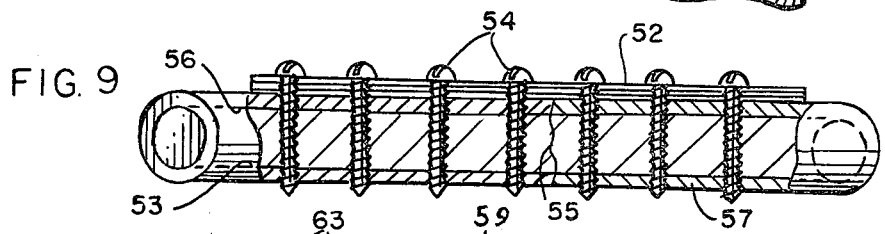
FIG. 9
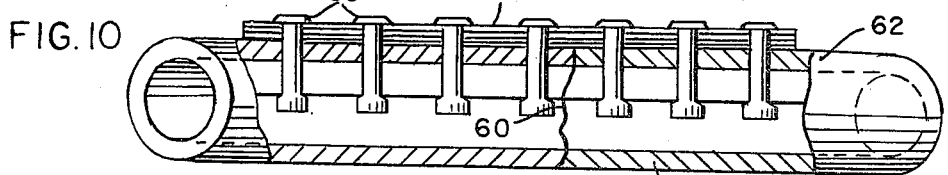
FIG. 10
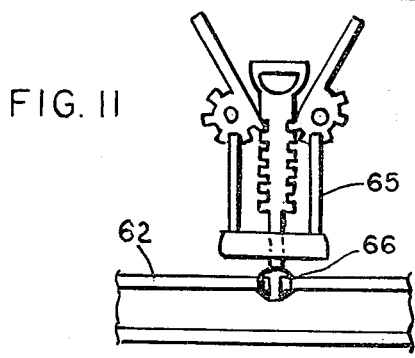
FIG. 11
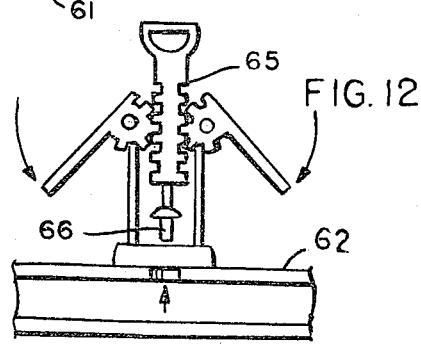
FIG. 12

INTERNAL FIXATION OF BONE, TENDON, AND LIGAMENTS

BACKGROUND AND SUMMARY

This invention relates to a method of obtaining fixation of different portions of the musculoskeletal system by a power driven fastening device.

Staples are currently used in orthopedic surgery for fixation of bones, for example, in osteotomy of the tibia. However, the staples are conventionally applied with a holder and are hammered into the bone. This allows for motion to occur at the site of staple insertion, loosening of the staple, and loss of firm fixation to the bone.

Staples are also being used to attach or reattach a ligament or a tendon to a bone. These staples are also hammered into the bone, and the same problem of motion loosens the attachment between the staple and the bone. This results in poor fixation of the tendon or ligament to the bone.

According to the invention, a power stable gun is used to drive the staple into bone quickly while minimizing the type of motion between the staple and bone which causes loosening of the staple. My method applies the staples easier, faster, and in a more secure manner than other methods and also minimizes the amount of cutting and stripping of soft tissue that is required before the staples can be driven. The method thereby reduces the risk of bone death, infection, and non-union of fractures and allows for fixation of bone fragments without an external fixation device. The power driven staples can be used for fixation of metaphyseal fractures, for arthrodesis or fusion of two bones, and for attachment of tendons or ligaments to bone. The invention also includes attaching a bone plate to a bone by a power rivet device. The rivets are fastened to only one cortex of the bone, and the plate can be attached quickly and without drilling through the other cortex.

DESCRIPTION OF THE DRAWING

The invention will be explained in conjunction with illustrative embodiments shown in the accompanying drawing, in which—

FIG. 1 is a fragmentary perspective view of the bones of the hand and wrist showing fixation of a fracture of the distal radius (wrist) and fixations of phalanges and metacarpals for arthrodesis of these bones;

FIG. 2 is a perspective view showing fixation of a metaphyseal fracture by a plurality of staples;

FIG. 3 is a fragmentary view showing the positioning of a power staple gun across a fracture preparatory to driving a staple into the bone;

FIG. 4 is an illustration of a joint which is to be fused after removal of bone and cartilage from the joint;

FIG. 5 shows the bones of FIG. 4 after bone and cartilage have been removed from the joint and staples have been driven into the bones for fixation;

FIG. 6 illustrates the use of power driven staples to affix a bone graft to bones to augment arthrodesis of the bones;

FIG. 7 shows a joint and a ligament which is to be attached to one of the bones of the joint;

FIG. 8 shows the ligament of FIG. 7 attached to the bone by power driven staples;

FIG. 9 illustrates a prior art method of attaching a bone plate to the diaphysis of a bone for fixation of a fracture of the bone;

FIG. 10 illustrates the attachment of a bone plate by rivets in accordance with the invention; and FIGS. 11 and 12 illustrate the removal of the rivets of FIG. 10.

DESCRIPTION OF SPECIFIC EMBODIMENTS

FIG. 1 illustrates the bones of a hand 15 and the radius 16 and ulna 17 of the arm. The hand includes metacarpals 18–22 and phalanges 23–27. The distal radius (wrist) 28 is fractured at 29, and the fractured portions are fixed and held together by a plurality of staples 30. The staples may be conventional U-shaped staples which include a pair of prongs which are driven into the bone on opposite sides of the fracture and a central connecting portion which extends between the prongs.

FIG. 2 is an enlarged fragmentary view showing fixation of a metaphyseal fracture 32 in a bone 33. A metaphyseal fracture is a fracture at the end of a bone where the cortex or dense bony outer layer of the bone is the thinnest. This portion of the bone can be easily penetrated by a power driven staple. A plurality of staples 34 are driven into the bone by a staple driving device such as a staple gun. The staples are applied generally perpendicularly to the fracture line so that one of the prongs of each staple extends into one of the bone fragments and the other prong of each staple extends into the other bone fragment.

FIG. 3 shows a conventional staple gun 36 being positioned against the bone 33 over the fracture 34 so that the staple extends perpendicularly to the fracture line and so that the prongs will be driven into the bone on opposite sides of the fracture. In one embodiment of the invention I used an Arrow Heavy Duty Model T-50 Staple Gun Tacker to drive Arrow P-50 9.52 mm staples into the bones of a cadaver. For clinical use biocompatible staples similar to staples which are currently being hammered into bones would be used. The Arrow staple gun drove the staples easily and securely into the bone. There was little or no lateral movement of the staples relative to the bone, i.e., movement which would cause loosening of the staples, and the staples were securely embedded in the bones to provide firm fixation of the fracture. This is in contrast to the method of hammering the staples into the bone, which causes movement between the staples and the bone which results in a loose securement of the staple.

Although I have described the use of conventional staples and a conventional staple gun for fixing the fracture, other fastening devices which can be power driven into the bone can be used, including fasteners which may add a compression force across the bones. The driving force can be provided by a spring, as in a conventional staple gun, compressed air, or other suitable means. The power driving device could be used with an interchangeable cartridge or magazine so that cartridges with different sizes and shapes of fasteners could be used as desired.

After reducing the fracture, i.e., bringing the ends of the bone together, the fasteners are powered across the fracture site to provide stabilization of the fracture. Common locations for usage of this type of fixation would be the distal radius (wrist), proximal ulna-olocranon (elbow), medial mallelous-tibia (ankle), and the ends of the finger bones—metacarpals and phalanges. Larger size staples or fastening devices could be used in the distal femur (lower thigh) and proximal tibia (upper leg bone). The method is applicable wherever the thickness of the cortical bone is such that it may be penetrated by a power-driven staple.

This method of fixation has several advantages. It is much easier and faster than any other method of fixation in current common usage. The method minimizes the amount of cutting and stripping of soft tissue (periosteum or bone covering), skin, and underlying tissue above the bone, thereby decreasing the risks of bone death, infection, and non-union of fractures. The method also permits fixation of bone fragments without the need for an external fixation device. For example, in fixation of the distal radius, the imminence of bone collapse is often such that an external fixation device is used to help prevent such collapse. These external fixation devices commonly exit through the skin and have the potential for various complications.

Fixation of bone by power driven staples also permits simple removal of the fixation devices. The staples can be removed with a conventional staple remover.

The invention also finds particular utility in arthrodesis. Arthrodesis is defined as the fusion of two bones by the elimination of the joint between them, thus creating one bone which is the length of the two bones minus the portion of the joint which was removed. To obtain such fusion, it is of paramount importance that the adjacent bones be held as immobile as possible where they are in contact to promote the growth of new bone to bridge them. Multiple devices have been used for fixation to accomplish such immobilization, including plates and screws, compression pins and devices, pins, and casts. In large joints, such fixation is usually reliable and relatively easy to apply. However, in small bones, e.g., phalanges, wrist, ankle, and foot, fixation is often very difficult because of the size of the structures involved. Plates and screws require large incision and stripping of tissue for their application. Crossed, parallel and looped wires do not give reproducible results, are often difficult to apply in the proper position, and often do not provide adequate immobilization of the bones.

The use of small staples which are driven into the bone by a power driving staple device presents a new method of obtaining fixation of the bond ends to permit fusion to occur. FIG. 4 illustrate a joint between a pair of bones 38 and 39 at which arthrodesis is desired. The joint is prepared for arthrodesis by removing the end portions 38A and 389A of the bones and the cartilage of the joint. The bone ends are then brought together in the desired position as shown in FIG. 5, and one or more staples 40 are power driven into the bones to achieve fixation. The use of a power driving device obtains immediate fixation and eliminates relative movement between the staples and the bones which would result in poor securement of the staple to the bone, and consequent motion between bone ends.

Referring again to FIG. 1, a staple 41 is used for fixation for arthrodesis of the metacarpal 18 and phalange 23, and staples 42 are used for fixation for arthrodesis between the metacarpals 20 and 21 and the carpus.

Arthrodesis of bone is sometimes augmented by the use of a bone graft to help promote the union of the two bones. Such a graft may also help in stabilization of the fusion site. FIG. 6 illustrates a pair of bones 43 and 44 which are fixed for arthrodesis and a bone graft 45 which is secured to both bones by power driven staples 46. Th bone graft is quickly and securely attached by the power driven staples.

During an operative procedure it is often necessary to attach or to reattach a ligament or a tendon to a bone. Hammer-driven staples are currently used for such attachment, but the aforementioned problem of loosening of the staple by the relative motion between the staple and the bone often results in poor fixation of the tendon or ligament to the bone. Referring to FIG. 7 the ligament 47 extending from the bone 48 is to be attached to the bone 49. FIG. 8 illustrates the ligament attached by a plurality of power driven staples 50. This method of attaching tendons and ligaments can be particularly useful in joint replacement surgery and ligamentous reconstructions after sports injuries.

The invention is also useful in securing bone holding plates to the diaphysis of bones for internal fixation of fractures. The diaphysis of a bone is the central or shaft portion of a long bone. Diaphyseal bone consists of a dense, thick, bony outer structure which has spongy bone or marrow within. In the internal fixation of fractures in the diaphysis, or surgical correction of such fractures, a bone plate is commonly affixed to the broken fragments by the use of screws. The screws used require either a tapped hole through the bone or must be self-tapping. In order to provide firm fixation of the bone plate, the screws usually go through both layers of dense bone. This is illustrated in FIG. 9 in which a bone plate 52 is secured to a diaphysis or bone shaft 53 by a plurality of screws 54. The bone plate extends across a fracture 55 in the bone, and the screws extend through both the upper and lower corticles or layers 56 and 57.

FIG. 10 illustrates my method of securing a bone plate to only one of the corticles by a power rivet device. In this method a bone plate 59 which is provided with a plurality of holes on each side of the fracture line 60 of a bone 61 is placed against the bone and holes are drilled through the upper cortex 62 in alignment with the holes in the plate. A plurality of rivets 63 are inserted through the openings in the plate and the cortex and secured by a conventional rivet gun. I have used a Master Mechanic Rivet Gun Kit Model K110-MM and the rivets packaged with the rivet gun to affix a four hole McLaughlin plate to the shaft of a human humerus. Such a rivet gun is described in detail in U.S. Pat. No. 3,154,210. Such rivets and rivet gun are commonly referred to as "pop rivets" and a "pop rivet gun". The fixation of the McLaughlin plate to the humerus was rigid enough so that after placement of four rivets the plate could not be pried from the bone. Such "pop rivets" can be used with either conventional, compression, or dynamic compression bone plates which are currently being used.

Fastening the bone plate with a power rivet gun provides several advantages. Only one cortex of the bone need be drilled, which reduces the possibility of weakening the bone by drilling two holes through the shaft at diametrically opposed locations. Since the plate is not attached by screws, the holes in the cortex need not be tapped. The plate can be attached more quickly and easily by the rivets than by conventional screws.

Current practice requires a rather large inventory of screw sizes in the operating suite. The use of "pop rivets" would permit replacement of this large inventory of screws with only a few different sizes of rivets.

FIGS. 11 and 12 illustrate one method for removing the rivets. A conventional corkscrew 65 is inserted into the rivet 66 as shown in FIG. 11, and the corkscrew is then retracted to withdraw the rivet from the bone.

FIG. 12 alternatively, the rivet can be drilled out using a surgical drillbit.

The pop rivet and rivet gun can also be used for attaching and reattaching ligaments to bone.

While in the foregoing specification detailed descriptions of specific embodiments of the invention were set forth for the purpose of illustration, it will be understood that many of the details hereingiven may be varied considerably by those skilled in the art without departing from the spirit and scope of the invention.

I claim:

1. A method of fixation for two portions of bone comprising the steps of:
   (a) holding the bone portions together;
   (b) placing a stapler over the bone portions;
   (c) activating the stapler to rapidly release stored energy;
   (d) rapidly and reproducibly imparting a controlled amount of the released energy to a staple thereby propelling the staple, the staple comprising at least a pair of prongs and means for connecting the prongs; and
   (e) guiding the propelled staple towards the bone portions whereby at least one prong of the staple is driven by momentum into and frictionally fits within each of the bone portions.

2. The method of claim 1 in which the two bone portions were formed from a single bone which was fractured to provide the bone portions.

3. The method of claim 1 in which the two bone portions are parts of two bones which are to be joined together and fused.

4. The method of claim 1 including the step of placing a bone graft over the bone portions before the power fastening device is placed over the bone portions, the fastening device being placed over the bone graft and the bone portions so that the fastener is driven through the bone graft and into the bone portions to affix the bone graft to the bone portions.

5. The method of claim 4 wherein the bone consists of metaphyseal-like bone.

6. A method of joining tendons or ligaments to bone comprising the steps of:
   (a) positioning the tendon or ligament against the bone;
   (b) placing a stapler over the tendon or ligament;
   (c) activating the stapler to rapidly release stored energy;
   (d) rapidly and reproducibly imparting a controlled amount of the released energy to a staple thereby propelling the staple, the staple comprising at least a pair of prongs and means for connecting the prongs; and
   (e) guiding the propelled staple towards the bone whereby at least one prong of the staple is driven by momentum into and frictionally fits within the bone and holds the tendon or ligament against the bone.

7. The method of claim 6 wherein the bone consists of metaphyseal-like bone.

8. A method of joining two portions of bone comprising the steps of:
   (a) holding the bone portions together;
   (b) placing a plate over the bone portions, the plate having at least one opening over each of the bone portions;
   (c) drilling a hole in each bone portion to align with a hole in the plate;
   (d) positioning a first rivet in a first opening in the plate and in a hole in one of the bone portions and activating a rivet gun to compress and deform the rivet adjacent said one bone portion to affix the plate to said one bone portion;
   (e) positioning a second rivet in a second opening in the plate and in a hole in the other bone portion and activating a rivet gun to compress and deform the second rivet adjacent said other bone portion to affix the plate to said other bone portion whereby the plate holds the two bone portions together.

9. The method of claim 8 in which each of the bone portions includes a shaft portion having a cortex, the hole in each bone portion being drilled through the cortex on only one side of the bone, the steps of positioning comprising extending each of the rivets through the cortex on only one side of the bone portion.

* * * * *